United States Patent [19]

Tessler et al.

[11] 4,027,674
[45] June 7, 1977

[54] METHOD AND DEVICE FOR REMOVING CONCRETIONS WITHIN HUMAN DUCTS

[76] Inventors: Arthur N. Tessler, 566 First Ave., New York, N.Y. 10016; Gerd Lupke; Manfred Lupke, both of 221 Rayette Road, Concord, Ontario, Canada, L4K1C7; Myron J. Tobias, 12 Dunsi mane Drive, Thornhill, Canada

[22] Filed: June 6, 1975

[21] Appl. No.: 584,672

[52] U.S. Cl. .............................................. 128/328
[51] Int. Cl.$^2$ ........................................ A61B 17/22
[58] Field of Search .................................... 128/328

[56] References Cited
UNITED STATES PATENTS

| | | | |
|---|---|---|---|
| 3,413,976 | 12/1968 | Roze | 128/328 |
| 3,785,382 | 1/1974 | Schmidt-Kloiber et al. | 128/328 |
| 3,902,499 | 9/1975 | Shene | 128/328 |

*Primary Examiner*—Channing L. Pace
*Attorney, Agent, or Firm*—David H. Semmes

[57] ABSTRACT

Method and device for catheterizaton within human ducts so as remove concretions, plaques or sclerotic clots, including generating exteriorally of the human body a series of high voltage pulses of sufficiently low amperage to avoid harm to human tissues, directing said pulses within an insulating medium into the human ducts to the situs of said concretions and selectively discharging sid pulses radially outwardly in order to impact across the surface of said concretions. A liquid may be flowed peripherally of discharging and against the concretion so as to achieve a hydroelectric cavitation. A suggested apparatus includes a pair of flexible electrodes insulated one from the other and co-terminating at the situs of the concretion. The positive electrode is positioned coaxially of the encircling negative electrode, such that the electrical discharging is radially outwardly from the positive electrode to the encircling surface of the negative electrode.

7 Claims, 6 Drawing Figures

METHOD AND DEVICE FOR REMOVING CONCRETIONS WITHIN HUMAN DUCTS

BACKGROUND OF THE INVENTION

FIELD OF THE INVENTION

Cystoscopy, particularly a method for removing concretions from the urinary tract, as well as placques and sclerotic clots within other human ducts. A principal difficulty in treatment within the urinary tract has been the inability of probing devices to reach the ureter or kidney. The suggested method and apparatus is of such diminutive diameter and flexibility to enable exploration and treatment in these critical areas.

DESCRIPTION OF THE PRIOR ART:

| | |
|---|---|
| West German | 847,950 |
| West German | 1,218,112 |
| West German | 1,284,561 |
| West German | 2,032,501 |
| Great Britain | 1,082,397 |
| Russian | 228,865 |
| ROZE | 3,413,976 |
| BALAEV | 3,543,757 |
| EDINY | 3,557,793 |
| SCHMIDT-KLOIBER | 3,785,382 |
| KLOZ | 3,792,701 |
| POHLMAN | 3,823,717 |
| ANTONEVICH | 3,830,240 |
| ANTONEVICH | 3,861,391 |

Roze, (corresponding to Russian Pat. No. 228,865 and West German Pat. No. 1,218,112) employs a long medicine needle, 5 of apparent inflexibility, having an enlarged boss 6 at its end. The negative electrode 3 is in the form of an enlarged, truncated head and in turn is encircled by envelope 7 and lacquer coating 8. An inner tube 4 separates the positive electrode 5 from the head or negative electrode 3, except for the protuberant boss portion 6 of the negative electrode. Water is discharged between the two electrodes. It is submitted that this construction is of such a wide diameter and inflexibility so as to preclude exploration into the ureter and kidney.

German Pat. No. 847,950 employs sonic vibrations to crush the stone, wherein glycerin is used as a lubricant upon the concretion. German Pat. No. 1,284,561 employs a lithotrite having electrodes and a pulse generator to supply instantaneous pulsing discharges, thereby creating hydraulic shock waves in a washing liquid which has filled the bladder. It is noted that this particular technology is also correspondingly exampled in British Patent Specification No. 1,082,397, Russian Pat. No. 228,865 and U.S. Pat. No. 3,543,757; all in the name of Balaev. Balaev employs a system wherein electrical oscillations are converted to ultrasonic oscillations within a fluid medium.

German Pat. No. 2,032,501 teaches a vibrating longitudinal probe, together with a connection for an irrigation device. Similarly, Ediny U.S. Pat. No. 3,557,793 is an improved structure for alternately using an ultrasonic mechanical oscillation together with a controlled hydraulic impact which is produced by an electric discharge in a liquid medium surrounding the concretion.

Schmidt-Kloiber U.S. Pat. No. 3,785,382 is particular to a miniaturized mechanically oscillatory device to facilitate concretion breakdown. The patentee employs a long, thin and apparently inflexible lithotriptor guided inside a thin ureter catheter 12, allowing passage of a rinsing liquid in the annulus therebetween. This device is purely mechanical in that the electrodes 7 produce shock waves in a separate chamber maintained external to the patient's body. Similarly, Kloz U.S. Pat. No. 3,792,701 includes a transducer which is maintained externally to the patient's body, together with a vibrating probe attached to a cystoscope that includes a flushing probe.

Pohlman U.S. Pat. No. 3,823,717 teaches a particular structure for an ultrasonic probe, including a plurality of cutting teeth around a hollow tubular device to allow withdrawal of disintegrated particles. The Antonevich U.S. patents transmit ultrasonic forces transversely through a catheter. The disclosure in both patents is identical; the claims of U.S. Pat. No. 3,861,391 being particular to subject matter which was divided out of the earlier U.S. Pat. No. 3,830,240. These patents suggest the use of miniaturized components so that even stones lodged high in the ureter can be fractured without the necessity of open surgery; noted as the present practice. The inventive feature of these patents comprises a wave guide to particularize the motion of a slender wire as it mechanically impacts upon the concretion, without any disclosed use of hydraulic action.

SUMMARY OF THE INVENTION

Method of removing concretions within human ducts comprising developing hydroelectric forces which are cavitated across the face of the concretions, including generating a series of high voltage pulses, directing said pulses to the situs of said concretions and selectively discharging said pulses radially outwardly across the surfaces of said concretions. Liquid may be flowed within an annulus peripherally of discharging, so as to achieve the desired hydroelectric cavitations upon the surface of the concretion. A suggested apparatus includes a flexible conduit of inert material having an axially positioned flexible positive electrode together with a flexible negative electrode embedded in the periphery of the conduit and terminating at the outer end of the conduit as a continuous surface, encircling and coextensive with the axial positive electrode. A high voltage, low amperage pulse generating apparatus is operatively connected to the positive electrode, such that electrical discharges radiate from said positive electrode radially outwardly to said encircling negative electrode.

DESCRIPTION OF THE PREFERRED EMBODIMENTS

Figure 1:
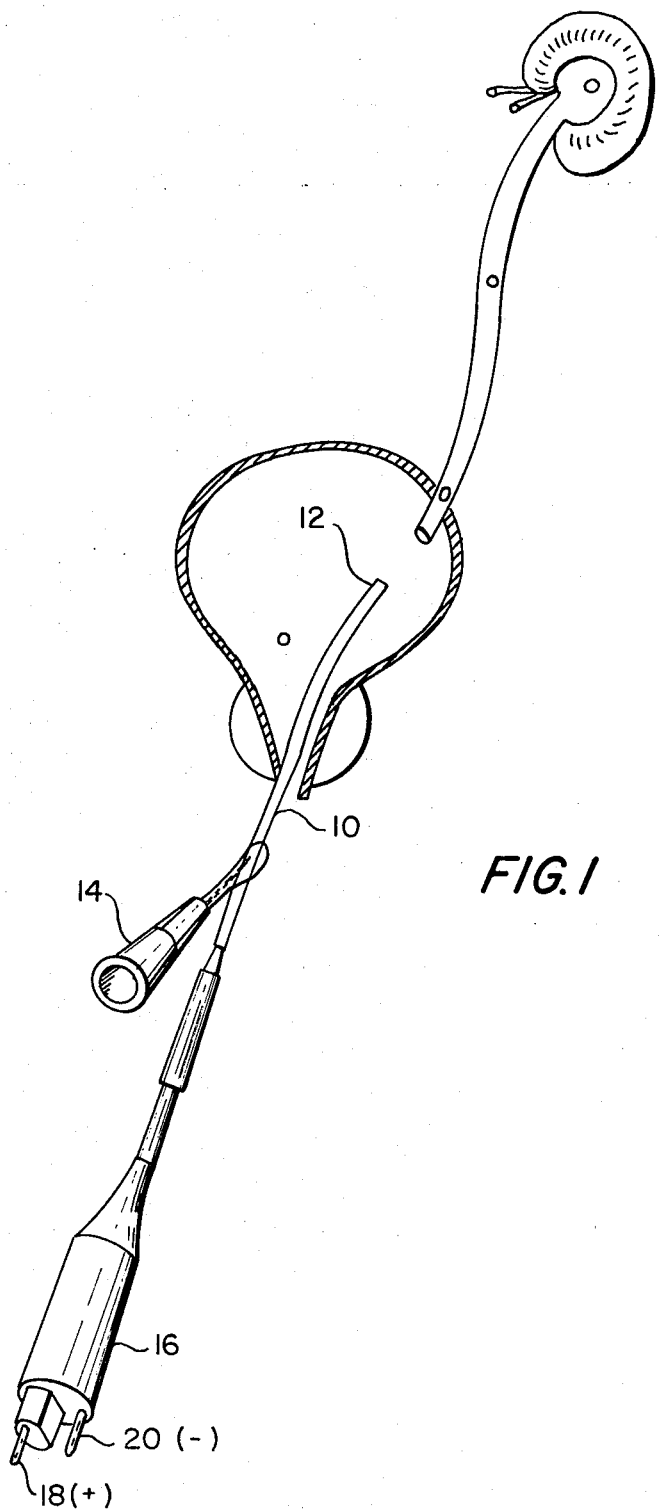
FIG. 1 is a schematic view, showing a suggested apparatus extending within the urinary tract to a concretion or stone in the ureter.
Figure 2:
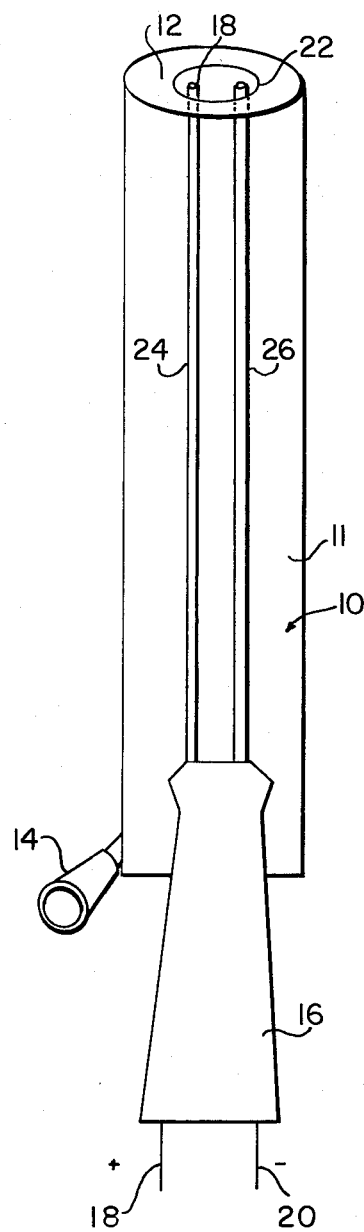
FIG. 2 is an enlarged, fragmentary side elevation of the device illustrated in FIG. 1, showing the negative electrode end 22 encircling the coaxially positioned positive electrode 18 with the liquid filled annulus 11 encircling both electrodes.
Figure 3:
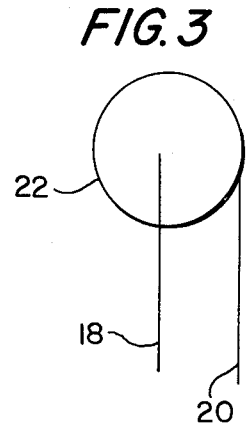
FIG. 3 is an enlarged fragmentary showing of the encircling negative electrode and positive electrode.

In FIG. 1 a suggested flexible catheterization device 10 is illustrated as extending into the urinary tract, such that its outer end 12 is positioned adjacent a uretal concretion. Device 10 defines an annulus 11 positioned about positive electrode 18 coaxially positioned within electrode 24 and negative electrode 20 positioned within insulating material 26 such that its outer end 22 peripherally encircles positive electrode 18 at the probe end 12 of the device. The device 10, as illustrated in FIG. 2 may define an annulus or hydraulic channel 11 which may be supplied by a syringe (not illustrated) fitted into nipple or valve attachment 14. The electrodes 18 and 20 may be connected to a pulse generating device of the type illustrated in FIG. 5 and including a 0-1 DC Milliamps Meter 30, an amperage adjusting knob 32, a pulse discharge or timing adjusting knob 34, electrode socket 36 and foot activated discharge switch 38.

Figure 5:
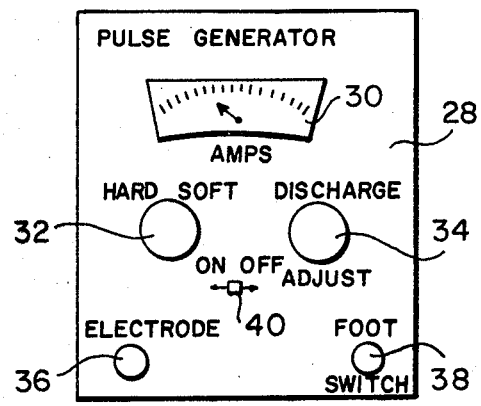
FIG. 5 is a front elevation of a pulse generating device of the type used for connection to the positive electrode.
Figure 6:
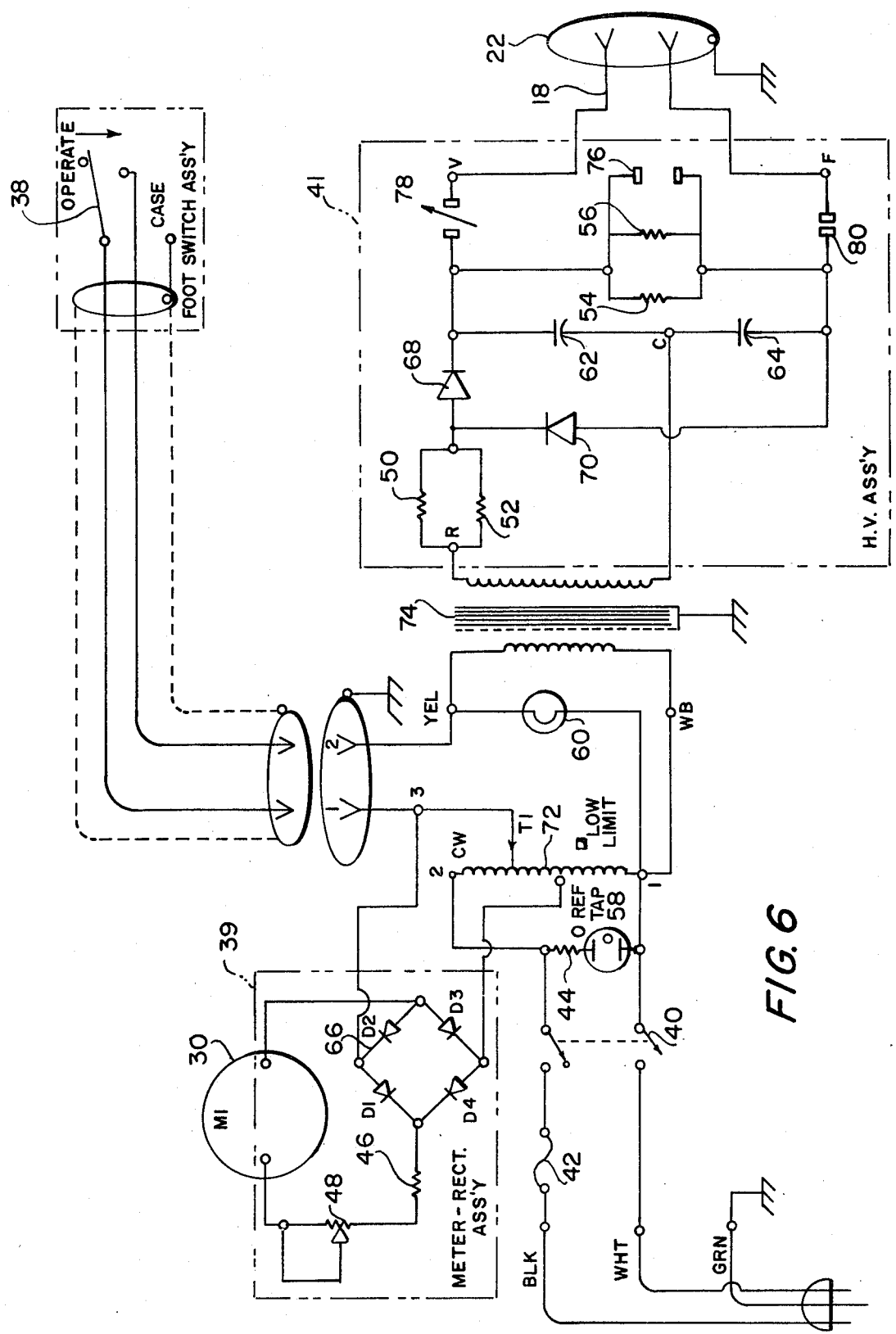
FIG. 6 is a circuit diagram of a proposed pulse generating apparatus.

In FIG. 5 a proposed circuit is illustrated as comprised of foot switch assembly 38, meter-rectifier assembly 39 and high voltage assembly 41.

In meter-rectifier assembly 39 there are included 0-1 DC milliamps meter 30, 50K ¼W resistor 46, 10K ¼W resistor 48 and Wheatstone bridge 66 comprised of individual 1 amp 200 PIV silicon diodes.

A 120 volt 2.25 amps variable transformer may be employed, together with a 3-amp slow blow 42, 47K ¼W resistor 44, NE51H glow lamp 58 and 120 volt incandescent lamp 60. A conventional double throw on-off switch 40 may be employed.

Adjacent the high voltage assembly 4' a 115 V-3000V.067 amps transformer (50 percent duty cycle max PRI leakage: 10 milliamps 75) may be employed, together with resistors 25K 50W resistors 50, 52; Amp 8000 PIV HP, HC rectifiers 58 and 70, resistors 12 Meg 2W Resistors 54, 56, 0.1 mf 5000WVDC Capacitors 62 and 64 as well as safety fixed spark gap 76, variable spark gap 78 and fixed isolation spark gap 80.

Figure 4:
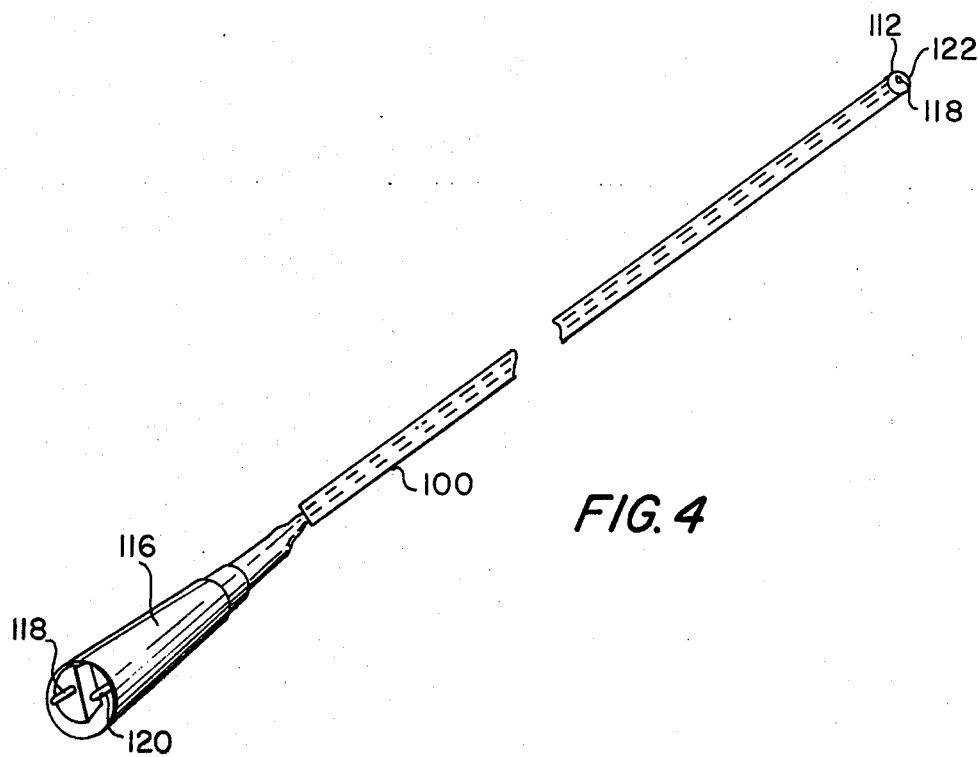
FIG. 4 is a fragmentary side elevation of a modified device absent the liquid supply conduit.

A modified form of the suggested apparatus is illustrated in FIG. 4 wherein the device 100 has a base 116 in which positive electrode 118 and negative electrode 120 are fitted at discharge end 112, negative electrode 122 extends in the periphery of the body of insulating material, encircles positive electrode 118 as at 122, such that the pulses are discharged radially outwardly from central electrode 118 to the encircling electrode 122.

The present method is designed for use not only within the ureter and kidney, but also within blood vessels, the common duct, the bioduct and the like and may be positioned by means of X-ray, fluroscopy or the like. A suggested voltage of 2-10K is recommended using intermittent direct current of less than 1 amp. The intermittent direct pulsing creates a shock wave with resultant cavitation of the liquid in the bladder or that liquid which has been infused via a conduit 11 for flowing across the concretion. Since the shock wave cannot compress the liquid, a cavitation is created which acts directly upon the surface of the concretion to be removed and without tissue damage. In the device illustrated in FIGS. 1 and 4 insulative material such as that trademarked Teflon may be employed for embedding the conductive electrodes.

Manifestly, the method may be varied and the suggested device altered without departing from the spirit and scope of the attached claims.

We claim:
1. Method for removing concretions within human ducts comprising:
   A. generating a series of high voltage pulses of sufficiently low amperage to avoid harm to human tissues;
   B. directing said pulses within an insulating medium extending into said ducts to the situs of said concretions; and
   C. selectively discharging said pulses radially outwardly across the surface of said concretions; and
   D. flowing a liquid peripherally of said discharging of pulses, so as to direct an hydroelectric impact against said concretions.

2. Method for removing concretions within human ducts as in claim 1, including directing said pulses within an insulating medium extending into the ureter and kidney.

3. Method for removing concretions within human ducts as in claim 1, including discharging said electrical pulses and flowing said liquid as a cavitation across the surface of said concretions.

4. Method for removing concretions within human ducts as in claim 3, including flowing said liquid at the interface of discharging electrical pulses upon said concretions.

5. A device for removing concretions within human ducts comprising:
   A. A flexible conduit of inert material extensible within said ducts to the situs of said concretions and including:
      i. a flexible positive electrode extending coaxially within said conduit and being embedded in electrically insulative material; and
      ii. a flexible negative electrode peripherally embedded in said conduit apart from said positive electrode and terminating at the outer end of said conduit, as a continuous electrically conductive surface encircling and coextensive with said positive electrode;
   B. A liquid carrying outer annulus supported peripherally with respect to said flexible conduit of inert material, such that liquid may be delivered simultaneously and coextensively with said electrical discharges, as hydroelectric cavitation upon said concretions; and
   C. a high voltage, low amperage pulse generating apparatus operatively connected to said positive electrode such that electrical discharges radiate from said positive electrode outwardly to said encircling negative electrode across the surface of said concretions.

6. A device for removing concretions within human ducts as in claim 5, said conduit being less than 1/16 inch in diameter.

7. A device for removing concretions within human ducts as in claim 5, said conduit being especially adapted for cystoscopy of the urinary tract and of sufficient length and so as to extend into the ureter and kidney.

* * * * *